United States Patent [19]

Kaplan et al.

[11] 4,151,065

[45] Apr. 24, 1979

[54] HORIZONTAL SLAB GEL ELECTROPHORESIS

[75] Inventors: Donald A. Kaplan, Topanga Canyon; Gary L. Wilcox, Malibu, both of Calif.

[73] Assignee: The Regents of the University of California, Berkeley, Calif.

[21] Appl. No.: 873,448

[22] Filed: Jan. 30, 1978

[51] Int. Cl.² ............... G01N 27/26; G01N 27/28
[52] U.S. Cl. ............... 204/299 R; 204/180 G; 23/230 B; 424/12
[58] Field of Search ............... 204/180 S, 180 G, 299; 23/230 B; 424/12

[56] References Cited

U.S. PATENT DOCUMENTS

| | | | |
|---|---|---|---|
| 3,773,647 | 11/1973 | Mandel et al. | 204/299 |
| 3,873,433 | 3/1975 | Seidel et al. | 204/180 G |

*Primary Examiner*—Arthur C. Prescott
*Attorney, Agent, or Firm*—Jessup & Beecher

[57] ABSTRACT

An improved horizontal slab gel electrophoresis apparatus having compartments for vertical wicks at each end of a removable horizontal trough. Adjacent to the vertical wicks are vertical buffer compartments with built in electrodes. A partition separates the vertical wirks from the buffer compartment and includes a slot with a silicone plug which can be removed after curing or hardening of the vertical wicks to permit communication between the buffer and the gel slab. Flow adapters and an interconnecting tube permit constant circulation of the buffer to maintain equal volume and pH. The horizontal trough has slots for insertion of combs to form up to seventy-five sample wells and additional slots at each end for sealing the end of the horizontal slab when the gel slab is removed. The apparatus includes coils in a horizontal bed or plate beneath the trough for cooling the gel slab during a run and levelling screws for levelling the horizontal trough before pouring the gel slab.

20 Claims, 7 Drawing Figures

HORIZONTAL SLAB GEL ELECTROPHORESIS

BACKGROUND OF THE INVENTION

This invention relates generally to methods and apparatus for electrophoresis and more particularly relates to horizontal slab gel electrophoresis.

The most commonly used technique for separation and purification of colloidal particles is by vertical gel electrophoresis using either tubes or slabs. However, certain problems are inherent with a vertical slab gel electrophoresis apparatus. For example, for obvious reasons it has been impossible to use very low percentage agarose gels that are necessary to separate high molecular weight fragments. For such resolutions gels of much less than 0.7% are necessary and cannot be used in a vertical slab gel electrophoresis apparatus. Also the thickness and therefore the capacities of vertical gels have been limited because thick gels are difficult to support and the number of samples per gel is small, usually no more than twenty-five.

Many of the above problems can be eliminated by the use of horizontal rather than a horizontal electrophoresis apparatus. While there have been horizontal slab gel electrophoresis devices described they also suffer from some deficiencies. Among these are that previous devices have not been able to accommodate the variable size gels and there has been no visualization or manipulation of the gels during operation. Further, the use of paper wicks for contact with a running buffer or coolant has been a disadvantage because the wicks can dry out, reducing the conductivity and sometimes even tear. Also, maintenance of the buffer equilibrium and pH as well as maintaining constant voltage have also been problems with prior art devices. One prior art device does provide a horizontal plate for a gel, but does not provide any easy method to remove the gel and appears to be unsuitable for very soft or low percentage gels. All of the above problems with the horizontal and vertical slab gel electrophoresis devices can be eliminated by use of the horizontal slab gel electrophresis device disclosed herein.

SUMMARY OF THE INVENTION

The purpose of the present invention is to provide an improved horizontal slab gel electrophoresis apparatus.

The present invention consists of a horizontal bed on which a removable trough or tray rests into which a horizontal slab gel can be poured. At the end of the trough are vertical chambers or compartments for forming vertical wicks of the agarose or acylamide gels which contact the horizontal slab. The vertical chamber is separated into two compartments by a partition with a buffer being in the compartment farthest from the horizontal slab in the trough. A removable silicone plug in a slot in the partition permits communication between the outermost compartments and the vertical wicks of gel. The outermost compartments are filled with a buffer which can be circulated through a tube connecting these compartments by a pump connected to flow adapters. Electrodes permanently installed in these compartments permit application of a voltage to opposite ends of the running buffer and therefore to the vertical and horizontal slabs of gel.

The removable trough or tray has vertical sides and open ends with handles provided for lifting the tray with the gel out of the apparatus after electrophoresis. The trough or tray has slots in the vertical sides for installation of combs to form up to seventy-five samples wells in three separate areas, as well as vertical slots in each end for installation of end plates to seal a gel slab. For very soft low percentage gels, the end plates can be inserted before lifting the tray. The tray is also made of an ultraviolet transmitting or transparent plastic, permitting viewing of the gel or sample run while still in the tray. The horizontal bed beneath the trough has grooves or coils through which a coolant can be circulated maintaining the horizontal slab gel temperature low during a run.

The device is set up by placing a levelling bulb in the approximate center of the tray when resting on the horizontal bed. The apparatus is then levelled by levelling screws at each end and at the rear of the center for this purpose. An agarose or acrylamide gel is then poured into the tray and the combs inserted to form sample wells. Preferably, the vertical gel wicks are poured prior to pouring the horizontal slab but may be formed simultaneously therewith by allowing the gel to run into the vertical compartments when forming the horizontal slab. After allowing the gel to cure for a period of time the combs are removed and the wells filled with samples. In some cases if the samples are very small, the wells may be prefilled with a running buffer and the samples layered underneath. The end compartments are filled with a buffer solution which is continuously circulated through an interconnecting tube and flow adapters by a peristaltic pump. Electrodes mounted in the buffer compartments conduct electricity to the gel through a slot in a partition separating the buffer compartment and the gel wick. After the gel has cured or hardened a plug in a partition separating the wick compartment from a buffer compartment is removed and the outer compartment filled with a buffer.

The horizontal slab gel trough or tray can be sectioned into lengthwise sections by longitudinal partitions permitting the simultaneous use of a variety of gel concentrations. A transparent plastic cover fits the top of the entire apparatus to prevent contamination and for safety purposes to prevent electrical shock while electrophoresis takes place.

It is one object of the present invention to provide a horizontal slab gel electrophoresis apparatus which incorporates vertical gel wicks.

Another object of the present invention is to provide a horizontal slab gel electrophoresis apparatus which permits easy removal of the gel after a run has been made.

Still another object of the present invention is to provide a horizontal slab gel electrophoresis apparatus which permits manipulation and visualization of the gel during a sample run.

Another object of the present invention is to provide a horizontal slab gel electrophoresis apparatus in which the size of the sample wells can be easily controlled.

Yet another object of the present invention is to provide a horizontal slab gel electrophoresis apparatus in which a buffer solution may be continuously circulated.

Still another object of the present invention is to provide a horizontal slab gel electrophoresis apparatus which permits direct cooling of the horizontal slab during a sample run.

Still another object of the present invention is to provide a horizontal slab gel electrophoresis apparatus which provides an improved method of contacting the gel with a running buffer.

Yet another object of the present invention is to provide a horizontal slab gel electrophoresis apparatus having a removable tray for easily removing the gel after a run.

Yet another object of the present invention is to provide a horizontal slab gel electrophoresis apparatus in which a removable tray is constructed of an ultraviolet transmitting material to permit viewing of the gel through the removable tray.

Other objects, advantages and novel features of the invention will become apparent from the following detailed description of the invention when considered in conjunction with the accompanying drawings wherein like reference numbers identify like parts throughout.

DESCRIPTION OF THE PREFERRED EMBODIMENT

Figure 1:
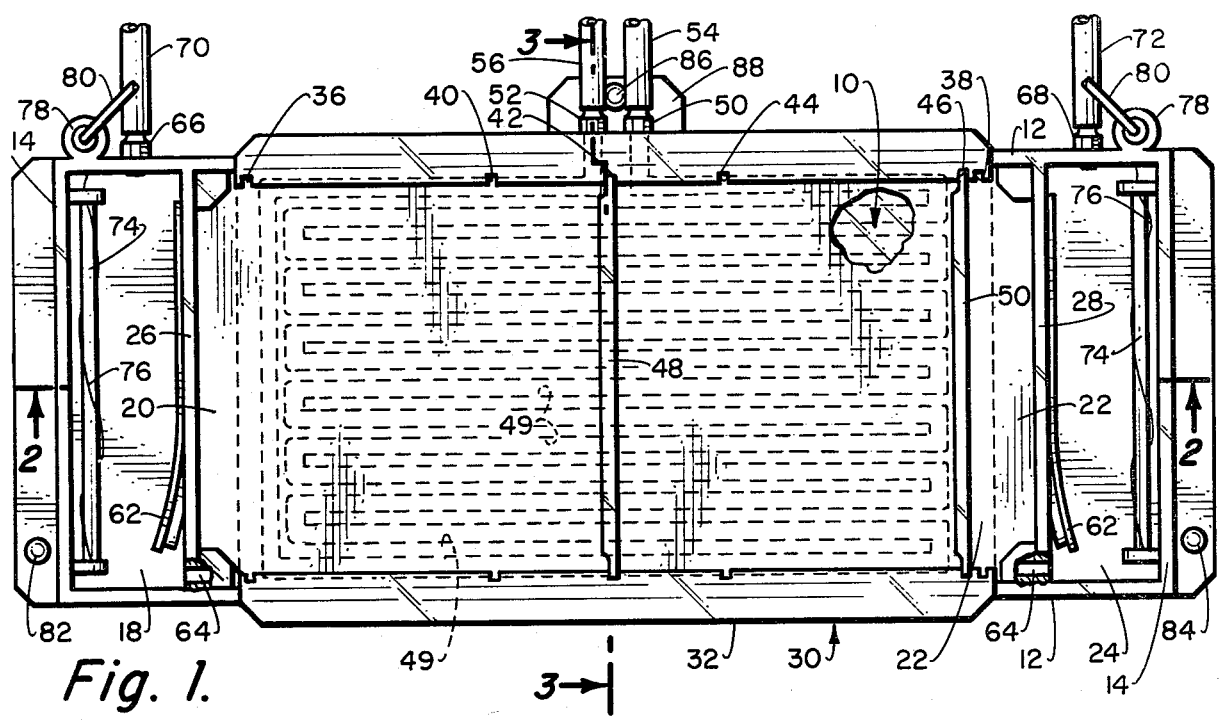
FIG. 1 is a top view with cover removed of a horizontal slab gel electrophoresis apparatus according to the invention.

The horizontal slab gel electrophoresis apparatus disclosed herein has many novel features that eliminate the problems of present gel devices described above. As can be seen in FIG. 1, (drawn with cover removed) the horizontal gel apparatus of the present invention has a horizontal bed 10 enclosed by a frame having sides 12, end plates 14 and bottom plates 16. The sides 12 and end plates 14 also enclose chambers at each end separated into compartments 18, 20, 22 and 24 by partitions 26 and 28. The sides 12, ends 14, bottom plates 16 and partition 28 are all secured together and sealed.

Resting on the horizontal bed 10 is a removable horizontal trough or tray 30 having borders 32 forming handles attached to the vertical sides 34. The trough is preferably constructed of an ultraviolet transmitting plastic such as clear UVT Plexiglas. The vertical sides 34 of the horizontal trough 30 have a plurality of spaced apart slots 36 and 38 on the ends for insertion of end plates for sealing and enclosing a gel in the tray and additional slots or grooves 40, 42, 44 and 46 for holding a selected number of combs such as 48 and 50 or solid guide plates (not shown). The particular grooves or slots selected for use depends upon the number of samples and spaces desired. For example, the spacing desired and illustrated in the drawings are two sets of twenty samples equally spaced.

The horizontal bed or plate 10 not only supports the horizontal trough 30 but also serves as a cooling block. The horizontal bed 10 is constructed of sheets of Plexiglas sandwiched together with one of the sheets having grooves 49 milled into the sheet. The grooves 49 provide a circulatory path for a coolant thus cooling the horizontal bed 10 and the horizontal trough 30. The coolant is supplied to the grooves or coils 48 by flow adapters 50 and 52 for attachment of hoses 54 and 56. Coolant can thus be circulated through the horizontal plate or bed 10 providing a great deal of cooling to the horizontal slab gel during a test run.

Figure 2:
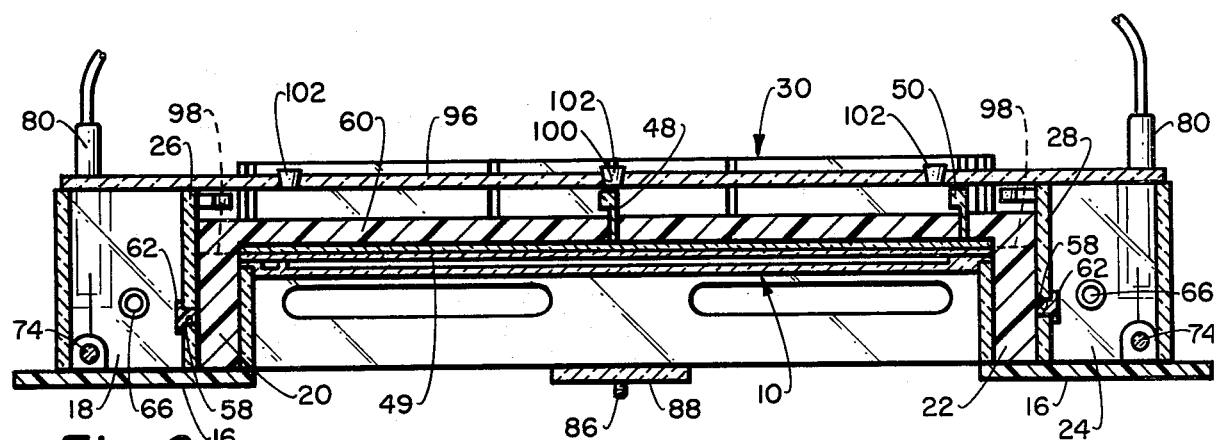
FIG. 2 is a sectional view of the horizontal slab gel electrophoresis apparatus taken at 2—2 of FIG. 1.
Figure 3:
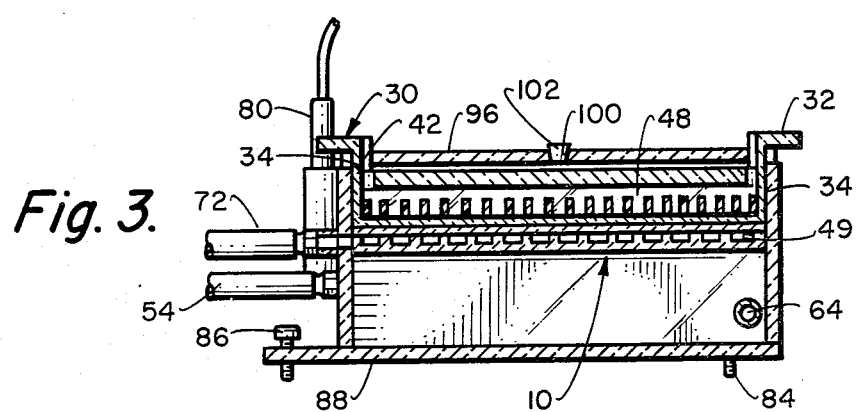
FIG. 3 is a sectional view taken at 3—3 of FIG. 1.

The end of the horizontal bed 10 and trough 30 terminate coincidentally at the transverse or crosswise vertical wells or compartments 20 and 22. These vertical wells 20 and 22 provide for a vertical wick of gel material in contact with the horizontal slab of gel as illustrated in FIG. 2. The vertical wicks of gel 60 are preferably poured prior to the pouring of the horizontal slab but may be poured simultaneously therewith. The partitions 26 and 28 separating the compartments 20 and 22 from compartments 18 and 24 have elongate slots 58 sealed by a removable silicone plug 62 while the gel is hardening.

After a gel is poured and hardened the plug 62 may be removed so that the vertical wick in compartments 20 and 22 may be in communication with wells or compartments 18 and 24. The compartments 18 and 24 are for a buffer and are interconnected by a tube 64 in order to maintain the pH and volume in the two buffer compartments equal. Buffer is circulated in the compartments 18 and 24 by a peristaltic pump (not shown) connected to the compartments by flow adapters 66 and 68 connected by means of hoses 70 and 72.

In many prior art devices electrical connections are made by simply inserting loose electrodes into the buffer solution. The present device, however, incorporates plastic rods 74 rigidly secured to the end walls 14 on which permanent electrodes 76, preferably platinum, are mounted. Sockets 78 attached to the outside of frame walls 12 are connected to the electrodes 76. The sockets 78 permit easy connection to the electrodes by male plugs 80 connected to a source of electricity (not shown).

Levelling screws 82, 84 and 86 are provided for levelling the trough 30 resting on the horizontal bed 10. The levelling screws 82 and 84 are on lips or flanges on the bottom pieces 16 while the levelling screw 86 is provided on a flange 88.

Before the horizontal slab of gel 60 is poured a level is placed in the middle of the trough 30 and the device or apparatus is levelled by levelling screws 82, 84 and 86.

Figure 4:
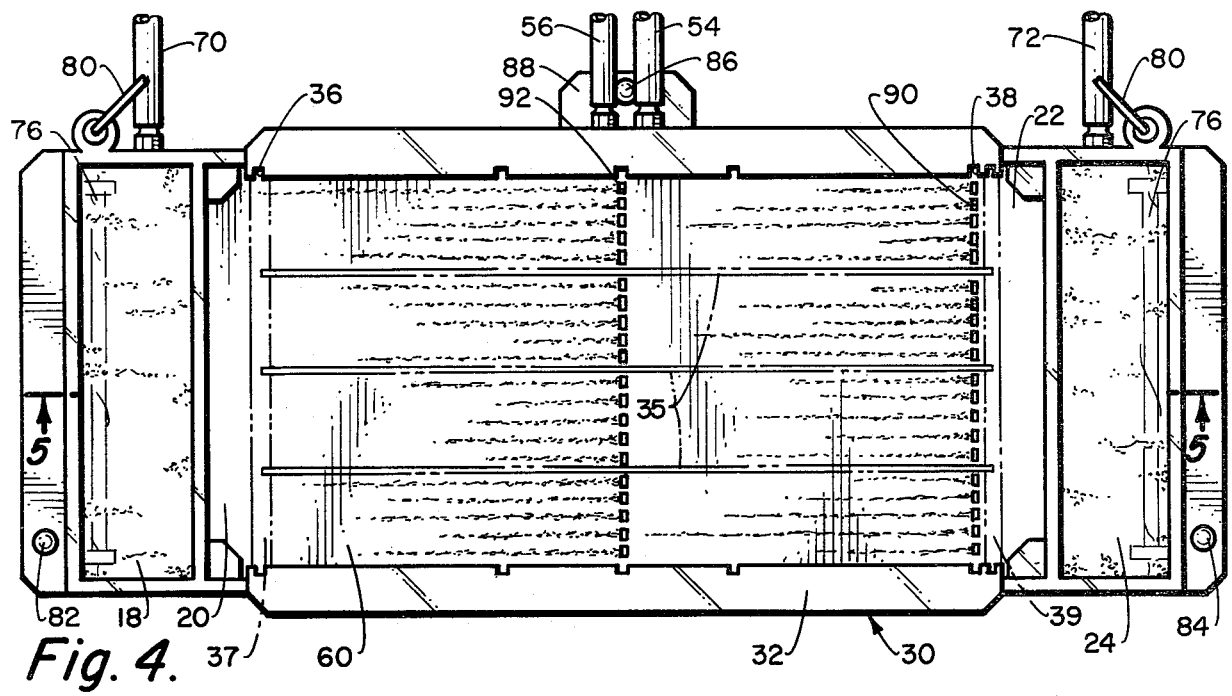
FIG. 4 is a top view with cover removed of the electrophoresis apparatus during a sample run.
Figure 5:
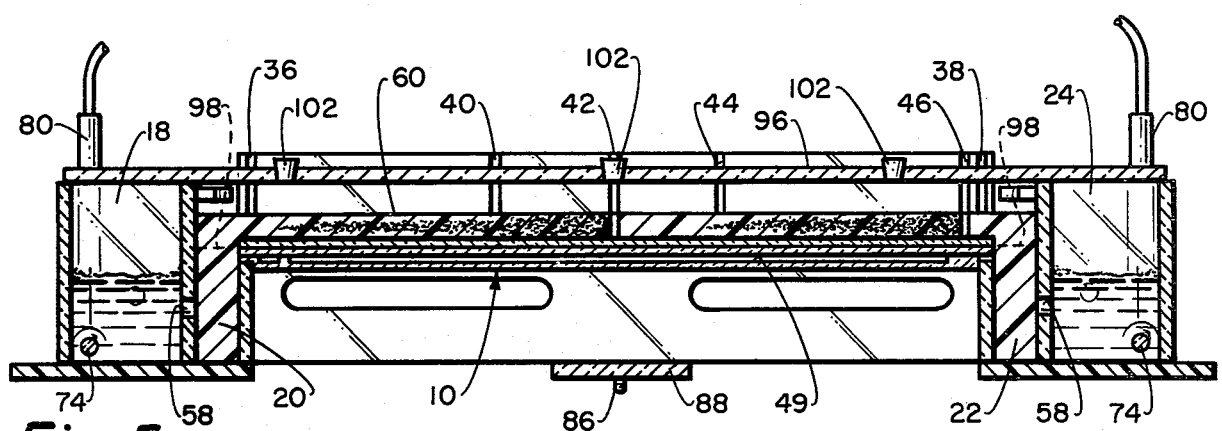
FIG. 5 is a sectional view taken at 5—5 of FIG. 4.

The preparation of the horizontal slab gel electrophoresis apparatus for running samples is illustrated in FIG. 4 (with cover removed), 5 and 6. The apparatus is set up as illustrated in FIG. 1 with the trough on tray 30 resting on the horizontal bed 10. Vertical wicks of gel 60 can be poured in the compartments 20 and 22 up to the level of the horizontal bed prior to insertion of the trough 30. While this is preferred, the trough 30 could be placed on the horizontal bed and the gel poured into the trough 30 and wells or compartment 20 and 22 simultaneously. However, pouring of the wicks in wells or compartments 20 and 22 first is preferred because the wicks can be different percentage gel than the horizontal slab gel.

After the horizontal slab of gel 60 has been poured into the trough 30, combs are inserted in selected grooves or slots 40, 42, 44 or 46 to produce the number of desired sample wells. In the drawings two combs 48 and 50 are illustrated producing twenty wells in two rows illustrated at 90 and 92 of FIG. 4. A cover 96 is then placed over the apparatus and the gel 60 is allowed to cure or harden. After the gel hardens the combs are removed producing two rows of sample wells 90 and 92 of twenty each. The ease of mounting the combs 48 and 50 permits very narrow sample wells to be produced and as many as twenty-five in each row have been utilized. Further, by using grooves 40, 44 and 46 as many as seventy-five samples can be tested in a single run. More or less channels could be provided within certain limits if desired.

In addition to the rows of samples illustrated the horizontal slab 60 could be partitioned along its entire length into several horizontal slabs as illustrated in phantom in FIG. 4 by means of lengthwise partitions 35 supported by cross bars 37 and 39 engaged in slots 36 and 38. This additional feature demonstrates the versatility of this device permitting the use of different percentage gels to compare the migration of fragments in these different gels.

After the gel hardens the combs 48 and 50 are removed and samples placed in each of the sample wells in the rows 90 and 92. If the samples are much smaller than the wells then the wells may be first filled with a buffer and the samples layered in beneath the surface of the buffer. The silicone plugs 62 are then removed from the slots 58 and the compartments 18 and 24 filled above the slots 58 with a buffer. The tube 64 permits the buffer to equalize in the two compartments 18 and 24 preventing any variation in the pH. A peristaltic pump (not shown) constantly circulates buffer in the wells 18 and 24 through hoses 70 and 72. A voltage is applied to electrode 76 in the buffer wells 18 and 24 through plugs 80 connected to a source of electricity (not shown).

Because preparative runs can require significant amounts of current which could result in heating of the horizontal slab of gel 60 in the trough 30, a coolant is circulated through the horizontal bed or plate by means of the hose connections 56 and 54 connected to the coils or grooves 49 in the horizontal bed. With this cooling block formed in the horizontal bed being used the gel slab 60 can be maintained as low as 5° centigrade. Maintaining this lower temperature is particularly important when using softer gels which have a watery consistency. The cover 96 covers the entire apparatus preventing evaporation and also for safety purposes.

Figure 6:
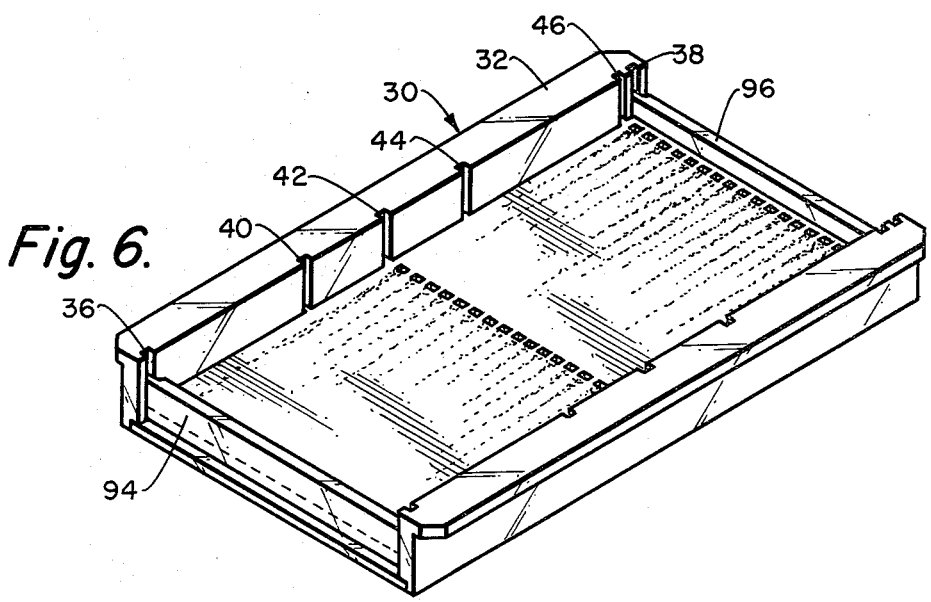
FIG. 6 is a view of the horizontal slab gel trough or tray removed from the apparatus.

When a run is completed the trough 30 can be lifted out of the device separating the connection of the horizontal slab of gel 60 with the wicks in the wells 20 and 22 as illustrated in FIG. 6. If the gel is of a soft, watery consistency then end plates 94 and 96 can be inserted prior to removal from the appararatus. In any event, end plates 94 and 96 can be inserted in the slots 36 and 38 respectively after removal of the tray to seal the gel in order to permit staining of the horizontal slab. The cover 96 is preferably constructed of Plexiglas and is placed over the electrophoresis apparatus when it is in operation. This has two purposes: first, it prevents dehydration of the gel 60 and second, it reduces the hazards of electrical shock.

The current from the buffer wells or compartments 18 and 24 is conducted to the horizontal trough 30 by vertical wicks of agarose or polyacrylamide gel in wells 20 and 22. As was indicated previously, the wicks are preferably poured prior to the pouring of the horizontal slab but both can be poured simultaneously. The vertical wicks are formed in the compartments or wells 20 and 22 sectioned or partitioned off from the buffer wells across 18 and 24. Direct contact of the adjacent wells or troughs 18, 20 and 22, 24 is permitted through the slots 58 which can be closed off by a removable silicone plug to separate two regions. Once the wicks of gel 60 have been poured and hardened the plugs 62 can be removed and the running buffer added to the compartments 18 and 24. The electrodes preferably platinum, are wound or wrapped around a plastic dowel 74 attached to the back end walls 14 of the buffer wells. The buffer is circulated from one well to the other by a peristaltic pump to maintain constant pH and ionic strength between the compartments. The hollow tube 64 connecting the two compartments maintains a constant volume between the compartments.

Figure 7:
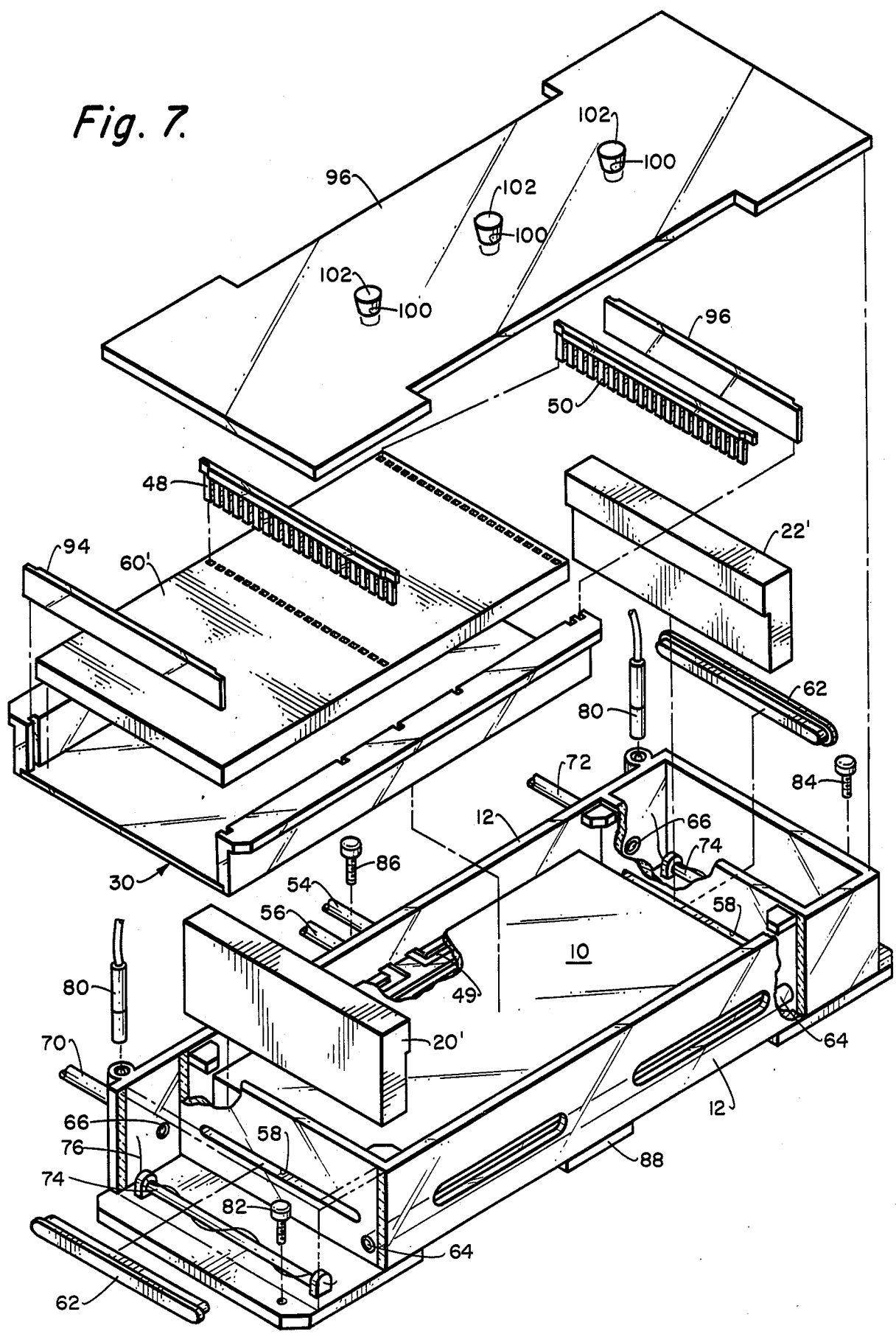
FIG. 7 is an exploded view illustrating the various features and functions of the apparatus from beginning to end of a run.

The sample wells in the rows 90 and 92 should be narrow to reduce the band width of the sample. The size of the sample wells can be very small and easily controlled because of the ease by which they can be formed by combs 48 and 50. The sample wells reach the bottom of the agarose or acrylamide gel without affecting the sample pattern. Samples are run into the gel at low voltage until the sample has entered the gel as determined by direct visualization. Once the sample has entered the gel the voltage can be increased. Samples have been run in 0.12 inch thick gels at 250 volts and 100 milliamps without distorting the fragment patterns. However, at this amperage it is necessary to keep the gel cool by circulating a coolant through the horizontal bed or cooling block 10 to maintain a constant temperature anywhere between 5° and 20° centigrade. The sample fragments are visualized by staining after the run. If the gel is stained prior to the run it is possible to visualize the fragments as they migrate through the gel. However, in a run without stain the trough is lifted out of the apparatus with the gel breaking the horizontal slab away from the vertical wicks as illustrated in FIG. 7. The shape of vertical wicks 20' and 22' are shown after the horizontal slab 60' has been lifted out with the trough 30 which can then be sealed by end plates 94 and 96 and stained.

The gel 60' can be stained directly in the trough 30 by sealing the end plates 94 and 96 with a suitable agarose or acrylamide gel. The slab of gel 60' then can be removed from the trough 30 and viewed by placing it directly on a long wave transilluminator or viewed directly through the trough 30 constructed of an ultraviolet transmitting material such as Plexiglas.

The electrophoresis apparatus is designed to accommodate either a large number of analytical samples or milligram quantities of fragments for preparative runs. The slots in the sides of the trough illustrated in FIG. 7 allow for placement of two or three combs of up to twenty-five teeth each giving a single gel a total capacity of up to seventy-five samples. In contrast to vertical gels where it is very difficult to remove the combs from low percentage agarose gels, the combs 48 and 50 can be removed with ease from gels down to 0.2% of agarose gel. Some samples run simultaneously in the seventy-five wells produce very reproducible patterns.

To allow for large preparative runs, the walls of the trough 30 were made relatively high (e.g., 1¾ inches). Using ½ inch thick agarose gel slabs (0.3, 0.5, 0.8, and 1.2%), good separation of samples was achieved. The use of very low percentage agarose gels facilitates the removal of samples.

The most distinctive features of this horizontal slab gel apparatus can be more clearly seen in FIG. 7. Among these is the use of the vertical agarose or polyacrylamide wicks 20' and 22'. With most instruments now in use a paper wick now connects the running buffer with the horizontal slab. These paper wicks tear easily, drying out during the run and are unable to carry the large electrical currents required for large preparative slabs. When the wicks 20' and 22' are poured first an interface illustrated at dotted lines 98 is produced between the horizontal slab and vertical wicks but does not effect electrical contact between these two slabs. At the end of each run the trough 30 is removed thereby separating the horizontal slab 60' from the vertical wicks 20' and 22'. Vertical wicks can be reused many times with some having been used for up to ten different runs without any apparent changes.

As was indicated previously, partitions (shown in phantom in FIG. 4) mounted in the trough 30 will allow simultaneous running of different percentage slabs, particularly those of agarose. At the ends of each trough 30 rectangular plates 37 and 39 can be inserted in the slots 36 and 38. The plates 37 and 39 would also include vertically cut slots which will hold dividers 35 running the length of the agarose trough. This will partition the gel bed into a number of sections with four having been successfully used. These compartments can be treated as individual slabs for running different comparison tests. This arrangement has been used to look at the relationship between molecular weight with different gels or agarose concentrations. It is also possible to study different agarose concentrations at the same time by using this appartus. In particular, agarose concentrations of 0.2, 0.4, 0.8 and 1.2 were simultaneously run. From this run the resolving power for high molecular weight fragments was determined.

When run with sample fragments of DNA (deoxyribonucleic acid) fragments in the lower percentage agarose the difference in migration rates is very pronounced for $10 \times 10^6$ restriction fragments of DNA and decreases for the $1.6 \times 10^6$ fragments. The increased migration rate is useful for rapid assay of restriction enzymes during their purification. The horizontal gel electrophoresis apparatus disclosed can be used analytically as well as preparatively. By using three combs instead of the two shown at 48 and 50 with twenty-five teeth, seventy-five samples can be run simultaneously or separately. These samples can be viewed as they run if a stain is incorporated into the gel or strained later without being removed from the trough 30. The cover 96 is also provided with openings 100 closed by stoppers 102 to permit the addition of any type of material such as a stain or gas before or duing a run.

For preparative runs, the horizontal gel is far superior to the vertical because thicker slabs can be poured and the percentage of agarose can be greatly reduced. Preparative gels containing as low as 0.2% agarose have been run. The greater yield of restriction fragments from the lower percentage gels is very useful.

The sectioning of the horizontal slab by lengthwise dividers gives the horizontal gel a versatility not obtainable with vertical gels. In a single run we were able to establish relationships between agarose concentrations and molecular weight. If a vertical gel apparatus were being used it would require four separate runs to obtain the same information. The design facilitates the use of vertical wicks, a most important design feature and provides an easy method of making contact with buffer wells or compartments because they eliminate the need for other modes of less convenient and reproducible current carriers. Further, the agarose or polyacrylamide wicks are reusable, are able to carry up to 200 milliamps and never dry out or produce current variations along the gel. Other important features of the invention are the removable trough, the cooling block to maintain a constant temperature in the gel during a run and the recirculation system for constant circulation of a running buffer.

Obviously, many modifications and variations of the present invention are possible in the light of the above teachings. It is therefore to be understood that the full scope of the invention is not limited to the details disclosed herein and may be practiced otherwise than specifically described.

We claim:

1. An apparatus for horizontal slab gel electrophoresis comprising:
   a horizontal flat bed,
   vertical chambers extending downward from opposite ends of said horizontal bed,
   a frame enclosing said bed and said chambers,
   partition means partitioning said vertical chambers into first compartments crosswise and immediately adjacent each end of said bed and second compartments parallel to and immediately adjacent said first compartments,
   an open-ended horizontal trough removably resting on said horizontal bed, and
   opening means for opening said first compartments for communication with said second compartments.

2. The apparatus according to claim 1 including:
   cooling means for cooling said horizontal bed.

3. The apparatus according to claim 2 wherein said horizontal bed and cooling means comprises:
   a first plastic sheet having continuous grooves therein,
   a second plastic sheet sealed over said first sheet for sandwiching in said grooves,
   flow adapters connected to said grooves for circulating a coolant therethrough,
   whereby said horizontal bed may be cooled by the coolant circulated through said grooves thereby cooling said removable trough.

4. The apparatus according to claim 1 wherein said opening means comprises:
   a removable silicone plug sealing an elongate slot in said partitioning means whereby the circulating buffer in one compartment may be in direct contact with a gel in the adjacent compartment when said plug is removed.

5. The apparatus according to claim 1 wherein said removable trough is made of an ultraviolet transmitting material whereby said trough having a gel therein may be removed from the apparatus and the gel can be directly illuminated through the trough.

6. The apparatus according to claim 5 including end plates for closing the ends of the removable trough to seal the ends of the gel in the trough.

7. The apparatus according to claim 5 wherein said horizontal bed is also constructed of an ultraviolet transmitting marerial.

8. The apparatus according to claim 1 wherein said removable trough includes:
   vertical sides, and
   a plurality of vertical slots in the vertical spaced at predetermined intervals along the sides of said trough.

9. The apparatus according to claim 7 wherein vertical slots are positioned at each end of said horizontal trough for insertion of end plates whereby the ends of said trough may be sealed when a gel is being removed.

10. The apparatus according to claim 1 including:

circulating means for circulating a buffer through said second compartments.

11. The apparatus according to claim 9 wherein said circulating means includes:
interconnecting conduit means connecting said second compartments whereby a buffer may be circulated from one of said second compartments through said interconnecting means to the other of said second compartments during a sample run.

12. The apparatus according to claim 1 including:
electrodes permanently mounted in each of said second compartments,
socket means on said frame connected to said electrodes whereby an electrical source can be connected to said electrodes.

13. The apparatus according to claim 6 wherein said trough and said horizontal bed are constructed of Plexiglas.

14. The apparatus according to claim 11 wherein said electrodes comprise:
a plastic rod traversing each of said second compartments,
a platinum electrode spirally wrapped around said plastic rods.

15. The apparatus according to claim 1 including:
adjusting means for adjusting said horizontal bed and said trough whereby said bed and said trough may be levelled.

16. The apparatus according to claim 1 including:
a transparent cover covering the entire apparatus including the vertical compartments, the horizontal bed and removable trough, said cover means being constructed of an ultraviolet transparent material.

17. The apparatus according to claim 15 wherein said cover is constructed of Plexiglas.

18. The apparatus according to claim 8 including:
at least one comb adapted to fit a slot in the sides of said trough,
said comb having a plurality of narrow teeth for forming narrow preformed wells in a gel poured into said trough.

19. The apparatus according to claim 17 wherein:
said trough has three pairs of slots spaced equally from one end of said trough,
a comb having twenty-five teeth fitting each of said slots for forming seventy-five sample wells.

20. The apparatus according to claim 9 wherein:
said end plates have a plurality of vertical slots,
sectioning means fitting said vertical slots for sectioning said trough into a plurality of longitudinal compartments,
whereby a plurality of different density gels may be simultaneously run with samples for comparison.

* * * * *